(12) United States Patent
Morrison et al.

(10) Patent No.: US 6,394,602 B1
(45) Date of Patent: May 28, 2002

(54) EYE TRACKING SYSTEM

(75) Inventors: Euan Morrison; Alan Edward Green, both of Cambridge (GB)

(73) Assignee: Leica Microsystems AG, Heerbrugg (CH)

(*) Notice: Subject to any disclaimer, the term of this patent is extended or adjusted under 35 U.S.C. 154(b) by 0 days.

(21) Appl. No.: 09/719,612

(22) PCT Filed: Jun. 16, 1999

(86) PCT No.: PCT/EP99/04175
§ 371 (c)(1),
(2), (4) Date: Dec. 14, 2000

(87) PCT Pub. No.: WO99/65381
PCT Pub. Date: Dec. 23, 1999

(30) Foreign Application Priority Data

Jun. 16, 1998 (GB) .............................. 9813041

(51) Int. Cl.⁷ ................................ A61B 3/14
(52) U.S. Cl. ...................................... 351/206
(58) Field of Search .................. 351/206, 209, 351/210, 214, 221; 359/630; 382/117

(56) References Cited

U.S. PATENT DOCUMENTS

| | | | |
|---|---|---|---|
| 5,214,455 A | 5/1993 | Penney et al. | 351/210 |
| 5,325,133 A | 6/1994 | Adachi | 351/209 |
| 5,365,302 A | 11/1994 | Kodama | 354/403 |
| 5,406,074 A | 4/1995 | Grisell | 250/221 |
| 5,712,684 A | 1/1998 | Inoue et al. | 348/341 |
| 5,982,555 A | * 11/1999 | Melville et al. | 359/630 |
| 6,154,321 A | * 11/2000 | Melville et al. | 359/630 |

FOREIGN PATENT DOCUMENTS

| | | |
|---|---|---|
| WO | WO 91/17695 | 11/1991 |
| WO | WO 95/31927 | 11/1995 |

OTHER PUBLICATIONS

S. F. Barrett et al., Digital tracking and control of retinal images, Optical Engineering, vol. 33, No. 1, Jan. 1994, pp. 150–159.
Joseph Jy–Haw Yu et al., Eye–Tracking System for Computer–Assisted Photocoagulation, Ophthalmic Surgery, vol. 22, No. 5, May 1991, pp. 260–265.
Jeffrey B. Mulligan, Image processing for improved eye–tracking accuracy, Behavior Research Methods, Instruments, & Computers, vol. 29, No. 1, 1997, pp. 54–65.

* cited by examiner

Primary Examiner—George Manuel
(74) Attorney, Agent, or Firm—Hodgson Russ LLP

(57) ABSTRACT

An optical instrument, such as a microscope or a camera, is provided for forming a viewable image of an object. The optical instrument comprises an objective lens for forming the viewable image at an image plane, an eye sensor for sensing the direction of gaze of a user viewing the viewable image and means for controlling a controllable function of the optical instrument in dependence upon the sensed direction of gaze. The eye sensor comprises a sensor lens for focusing light reflected from the retina of the user, an imaging transducer located at a plane which is conjugate to the image plane with respect to the sensor lens, for generating an electrical image sign of a portion of the user's retina, a memory for storing retinal image information of the user and circuitry for comparing the retinal image signal generated by the imaging transducer with the stored retinal image information to generate gaze information indicative of the direction of gaze of the user.

42 Claims, 9 Drawing Sheets

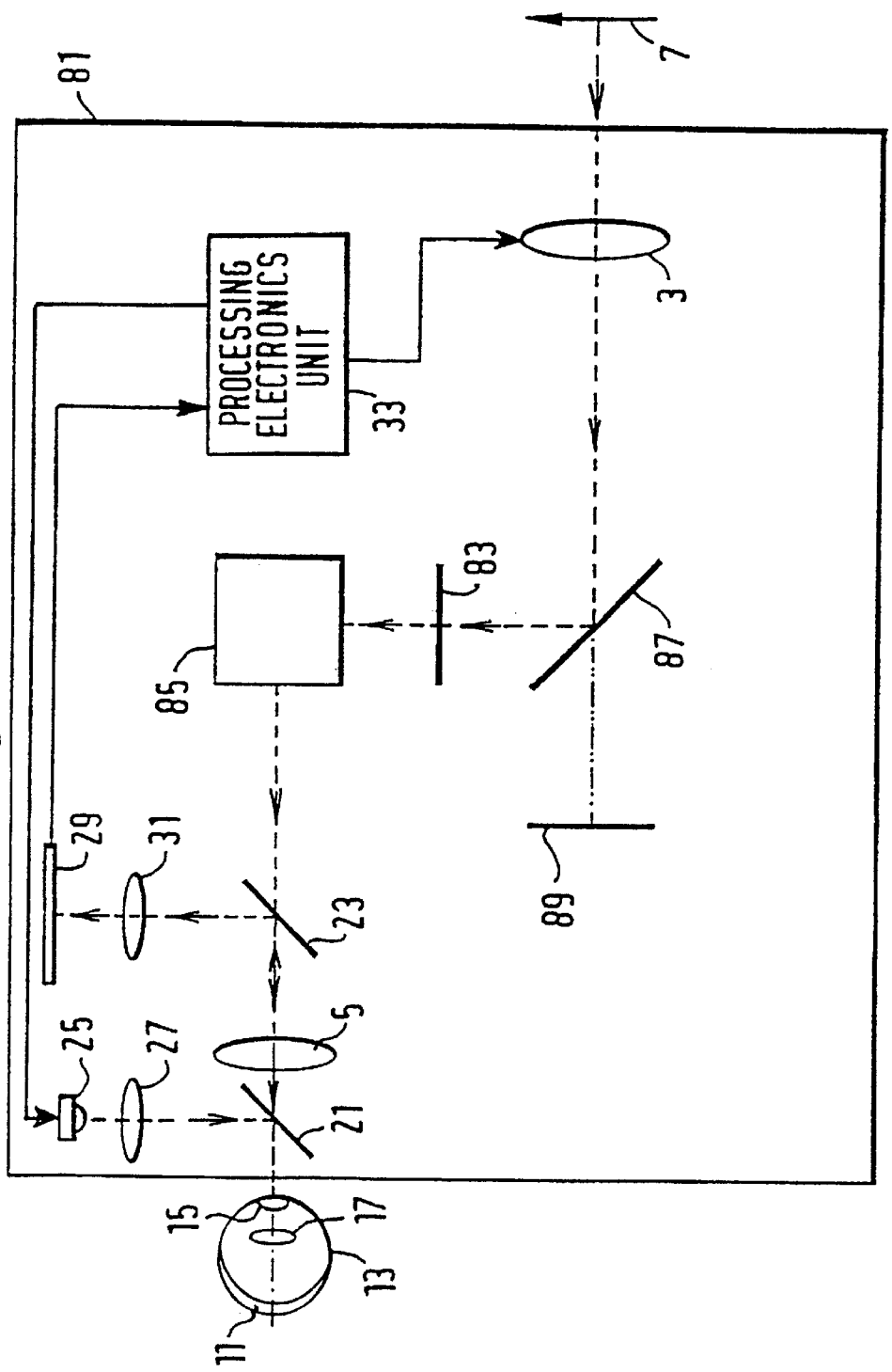

EYE TRACKING SYSTEM

The present invention relates to an apparatus and method for tracking the direction of a user's gaze. The invention has particular relevance to an eye tracking system for use with optical instruments which form a viewable image of an object, such as microscopes, cameras, telescopes etc.

The applicant has already proposed in the PCT patent application PCT/EP 95/04178 an in the publication WO96/13743 a microscope system which employs eye tracking techniques to track the position of gaze of a user viewing an image through a microscope eyepiece, which gaze information is used to controls for example, an auto-focus system. This is particularly useful at high magnification, where the depth of field is often limited and only a small part of the total field of view is in sharp focus at any one time. This earlier patent also teaches that the gaze information can be used to control other function of the microscope, including hands-free movement of the microscope or the operation of a menu-driven computer system superimposed on the user's normal field of view. for eye tracking. The two most common of these are Limbus trackers and video eye trackers.

Limbus trackers usually operate by illuminating the user's, eye, typically with one or more infra-red LEDs and detecting the light reflected off the white of the eye (sclera) using one or more photodetectors. Since the amount of light reflected off the white of the eye will vary depending on the position of the dark regions (the pupil and the iris), it is possible to determine where in the specified field of view the user is actually looking. However, this type of eye tracking system cannot unambiguously determine the angle of gaze because it only gives information relating to the position of the iris-sclera boundary. In addition, whilst Limbus tracking techniques give fairly good information on the horizontal position of the surface of the eye, they cannot accurately determine the vertical position due to obstruction from eyelashes and eyelids.

There are many different video-based eye tracking techniques. Some of these simply illuminate the eye and view the pupil using an imaging system. By determining the centre of the pupil from the image, information relating to the pointing direction of the eye can be obtained. This technique, however, suffers from the problem that movements of the observer's head cannot be distinguished from movements of the eye.

Other more sophisticated video-based eye tracking systems have been proposed which detect the position of the Purkinje images, which are the reflections of the illumination source off the surfaces of the cornea and the lens (often referred to as the highlights or glints) Whilst this technique is relatively accurate because it is independent of head movements, it suffers from the problem that some of the Purkinje images are extremely weak and therefore difficult to image clearly.

One aim of the present invention is to provide a different, accurate eye tracking technique for use with optical instruments which form a viewable image of an object, such as microscopes, cameras and the like.

According to one aspect, the present invention provides a new eye tracking system instrument in general and an optical instrument for forming a viewable image of an object comprising: an objective lens for forming a viewable image of the object at an image plane; an eye sensor for sensing a direction of gaze of a user viewing the viewable image; and means for controlling a controllable function of the optical instrument in dependence upon the sensed direction of gaze; characterised in that the eye sensor comprises: (i) a sensor lens for focusing light reflected from the retina of the user; (ii) an imaging transducer located at a plane which, when the user views said viewable image, is commonly conjugate with said image plane to the retina of the user's eye, for generating an electrical image signal of the portion of the user's retina which can be seen through said sensor lens; (iii) a memory for storing retinal information; and (iv) comparing means for comparing signals representative of the retinal image signal generated by said imaging transducer with said stored retinal information to generate gaze information indicative of the direction of gaze of the user. This system has the advantage that the direction of gaze determined by the eye sensor is independent of any movement of the user's head.

Preferably, one or more eyepieces are provided to facilitate the viewing of said viewable image. In a preferred form of the instrument, an illumination source is provided for illuminating the retina of the user's eye in order to improve the quality of the retinal image generated by the imaging transducer. Preferably the illumination source has a number of light emitting portions which are arranged off the optical axis so that selected ones of the light emitting portions can be illuminated at any one time in order to avoid the effects of cornea glints.

Exemplary embodiments of the present invention will now be described with reference to the accompanying drawings in which:

FIG. 3b is a line drawing of the part of the user's retina shown in FIG. 3a which is generated by processing the image shown in FIG. 3a;

FIG. 9 is a schematic, diagram of a camera embodying the present invention.

Figure 1:
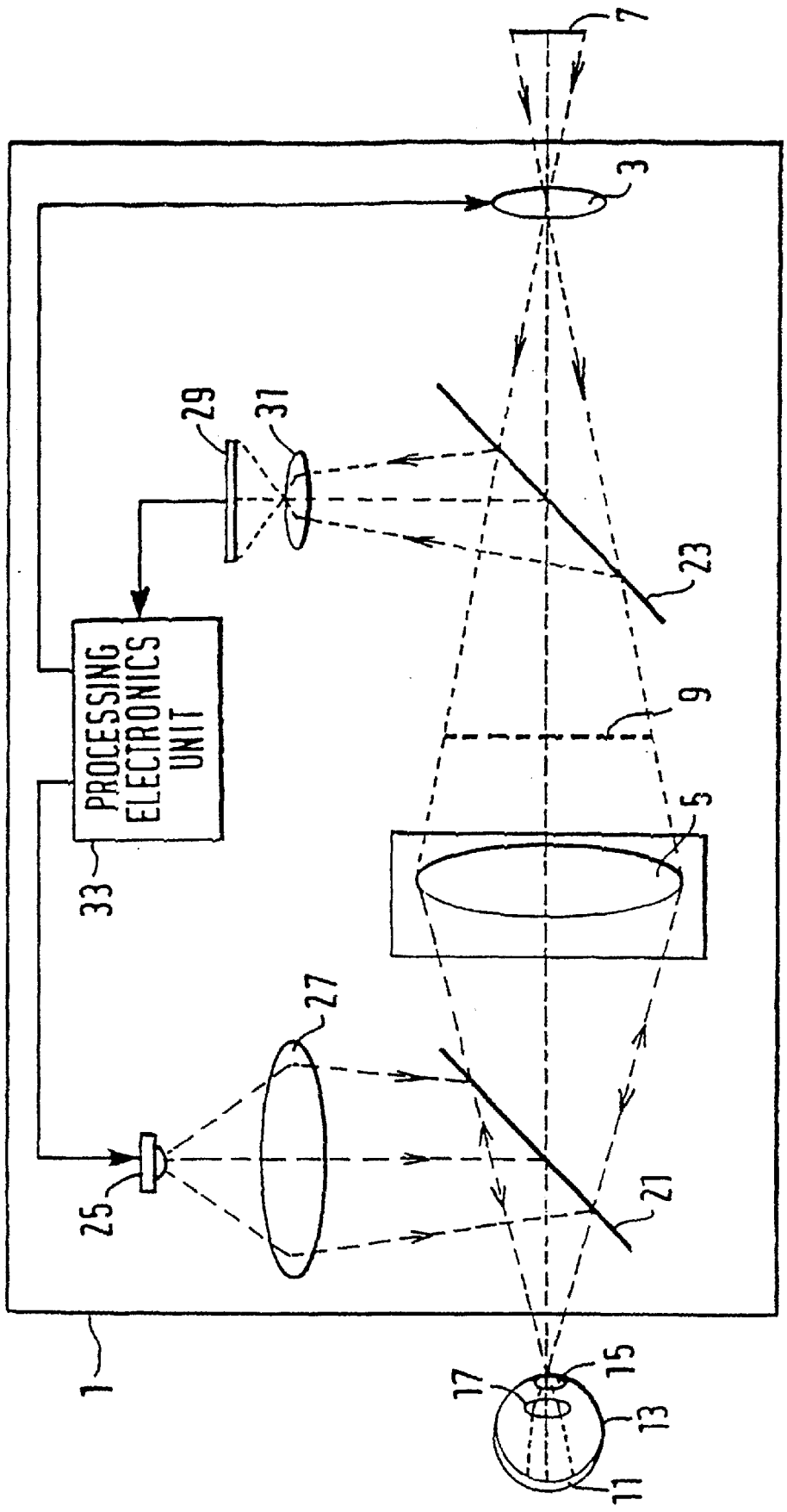
FIG. 1 is a schematic diagram illustrating the principal components of a surgical microscope embodying the present invention.

FIG. 1 is a schematic diagram of a surgical microscope 1. The microscope 1 comprises an objective lens 3 and an eyepiece 5, both of which are illustrated schematically by a single lens but which will, in practice, comprise a number of lenses and in addition eventually zoom lenses or the like. The objective lens 3 operates to generate an image of an object 7 being examined at an intermediate image plane, illustrated by the dashed line 9. This image is then focused by the eyepiece 5, the cornea 15 and the eye lens 17 onto the retina 11 of the observer's eye 13.

As shown in FIG. 1, in this embodiment, the microscope 1 also comprises two beam splitters 21 and 23 located along the optical axis of the microscope 1. Beam splitter 21 operates to reflect light of a suitable wavelength preferably in the unvisible range from an illumination source 25 onto the retina 11 of the observer's eye 13. A lens 27 may be provided between the illumination source 25 and the beam splitter 21 for focusing the light from the source 25 onto the cornea 15 of the eye 13. By the preferred focusing on the cornea 15 of the eye 13 rather than the retina directly, a larger part of the retina 11 is illuminated due to the action of the eye lens 17. Some of this illumination light is reflected from the surface of the retina 11 back through the eye lens 17 and cornea 15 to the beam splitter 21, where part of the reflected light is reflected back to the source 25 and the rest passes through to the eyepiece 5. Since the eye 13 is focused on the intermediate image plane 9 (to view the image of the object 7 formed by the objective lens 3), the eye lens 17 and the eyepiece 5 operate to form an image of the illuminated part of the retina 11 at the intermediate image plane 9. This retinal image is then reflected by the beam splitter 23 and focused onto a sensor 29—preferably a CCD-sensor or the like—by lens 31. As shown in FIG. 1, the image generated by the sensor 29 is input to a processing electronics unit 33, which is operable, in this embodiment, to process the received retinal image to determine the observer's direction of gaze and to control the auto-focusing of the objective lens 3 in response thereto. In this embodiment, the system can identify the direction of gaze at a resolution of—for example 30 "pixels" by 30 "pixels" over, the full field of view of the microscope. In other words, it outputs an x,y coordinate in the range (0,0) to (29,29), representing the "pixel" which the observer is looking at.

Figure 2:
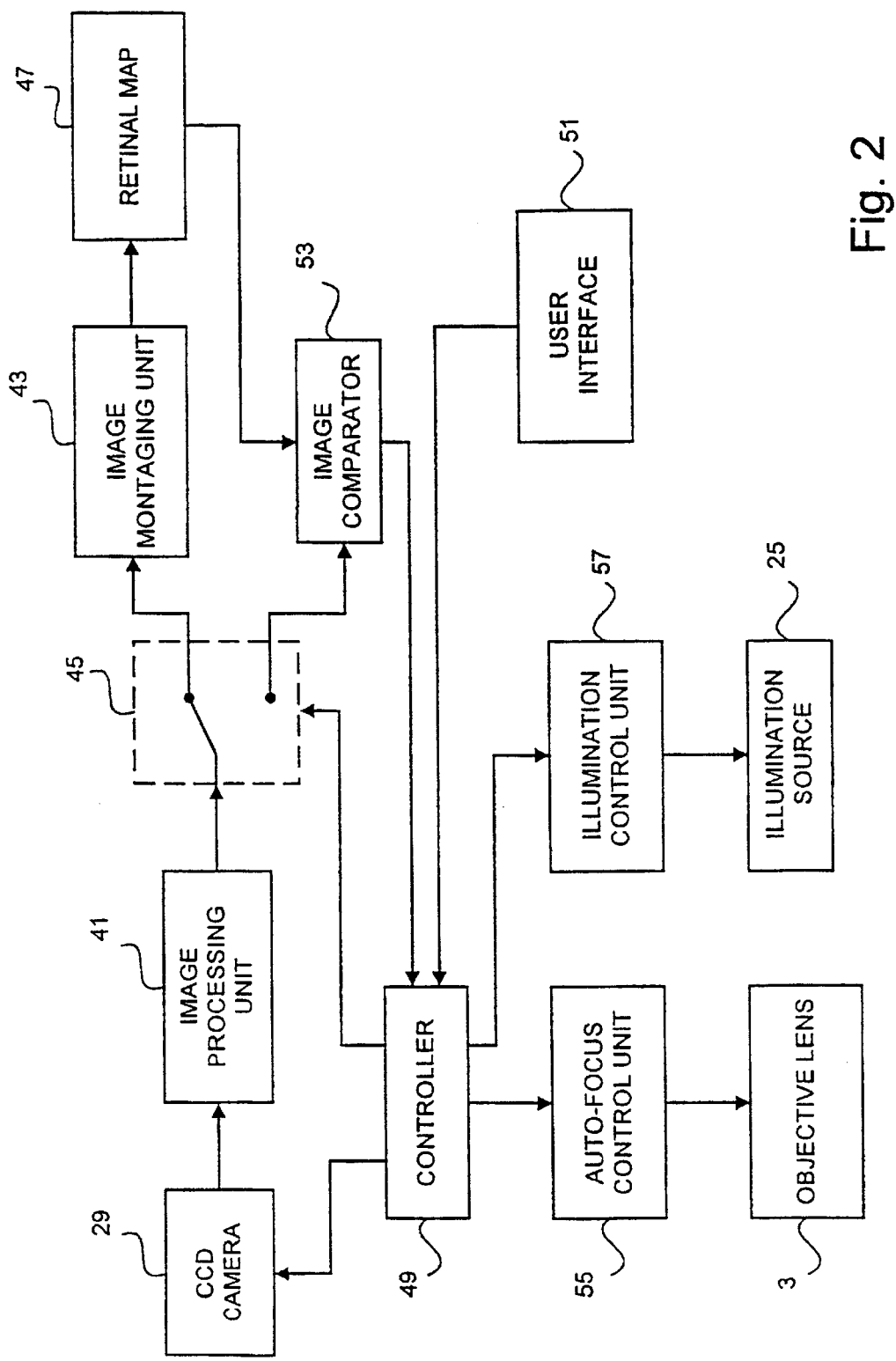
FIG. 2 is a block diagram illustrating the electronic components of the microscope shown in FIG. 1.
Figure 3A:
FIG. 3a is a two-dimensional image showing part of a user's retina which is generated by a sensor forming part of the microscope shown in FIG. 1.
Figure 3B:
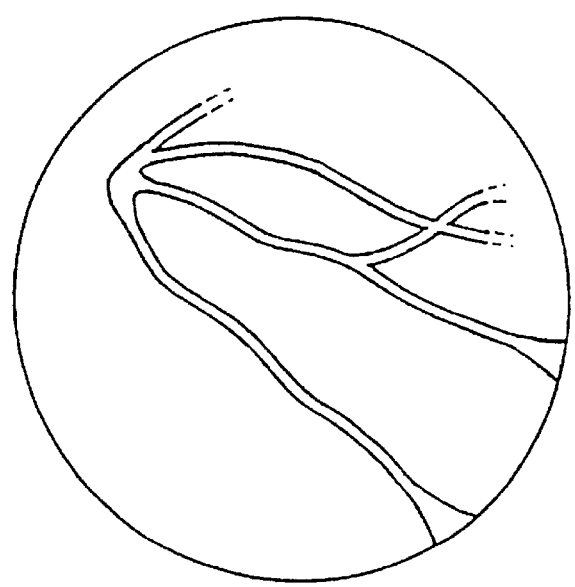
Figure 3C:
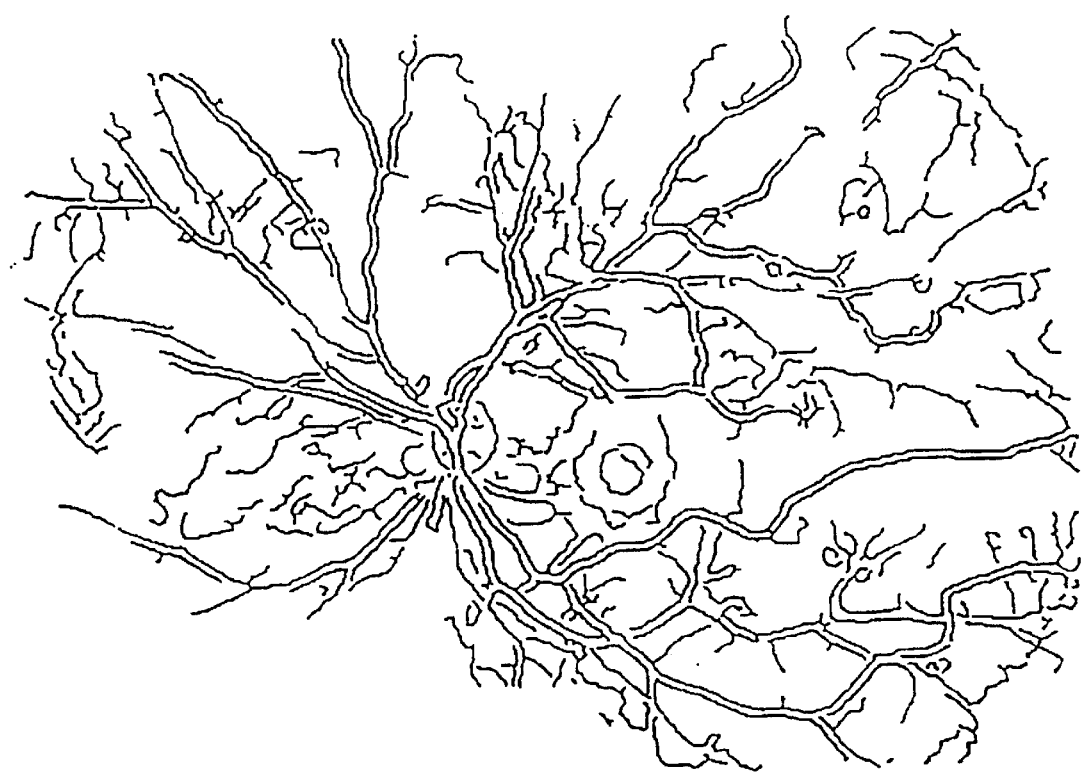
FIG. 3c is a line drawing of the entire surface of a user's retina obtained by montaging retinal images which are generated when the user is looking at a number of preselected points.
Figure 4:
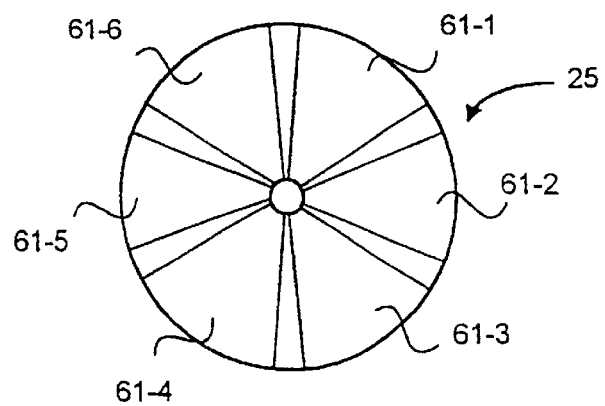
FIG. 4 is a schematic diagram of an illumination source used to illuminate the user's eye in the first embodiment.

The way in which the system determines the observer's direction of gaze in this embodiment will now be described with reference to FIGS. 2 to 4. FIG. 2 is a block diagram illustrating the principal components of the eye tracking system used in the present embodiment to determine the observer direction of gaze. As shown, the sensor 29 is connected to an image processing unit 41, which processes the retinal image generated by the sensor 29 to highlight characteristic features in the retinal image. In this embodiment, the features which are highlighted are blood vessels, since these are relatively easy to find and highlight using standard image processing edge detection techniques. Details of appropriate processing algorithms which—for example—can be used can be found in the paper entitled "Image Processing for Improved eye Tracking Accuracy" by Mulligen and published in 1997 in Behaviour Research methods, Instrumentation and Computers, the content of which is incorporated herein by reference. FIG. 3a shows a 2D image output by the sensor 29 after some filtering to remove low frequency intensity variations present in the original retinal image (not shown). As shown, the fine structure and detail of the retina surface are clearly visible. This retinal image is then processed by the image processing unit 41 to generate a corresponding black and white line drawing, which is illustrated in FIG. 3b. As shown in FIG. 3b, in this embodiment, only the detail of the blood vessels remains after processing by the processing unit 41.

As those skilled in the art will appreciate, as the observer's gaze moves over the object 7 being viewed, the retinal image which is generated by the sensor 29 will change. Therefore, by getting the observer to look at a plurality of points scattered over the field of view and by obtaining a sensor image, e.g. a CCD image of the retina when the observer is looking at each of the points, a "map" of the observer's retina 11 can be determined. In this embodiment, this mapping of the observer's retina 11 is performed when the microscope is in a calibration mode of operation. When the microscope is then in its normal mode of operation, the observer's direction of gaze can be determined by comparing the current retinal image generated by the sensor 29 with the retinal map generated during the calibration stage.

As shown in FIG. 2, a controller 49 is provided which operates to control the above described modes of operation of the microscope 1. In particular, in response to a calibration request, input by a new observer via a user interface 51, the controller 49 controls the position of the switch 41, so that the image processing unit 41 is connected to the image montaging unit 43. In this embodiment, during the calibration stage, a test card (not shown) is provided as the object to be viewed under the microscope 1, which card has a number of visible dots arrayed over the field of view. The new observer is then directed to look at each of the dots in turn. As he does so, the montaging unit 43 receives the retinal images generated by the sensor 29 and "joins" them together to form a map 47 of the new observer's retinal surface 11. FIG. 3c shows the resulting retinal map 47 generated for one observer. This retinal map is then stored in a memory (not shown) for use when the microscope 1 is in its normal mode of operation.

After the calibration stage is complete, the controller 49 causes the microscope to return to its normal mode of operation, by connecting the image processing unit 41 to the image comparator 53, via the switch 45. During this normal mode of operation, the sensor 29 generates an image of the part of the observer's retina 11 which the sensor 29 can currently see. This retinal image is then processed by the processing unit 41 in the manner described above, to generate a line drawing of the fine structure of the retinal surface. This line drawing is then passed to the image comparator 53, where it is compared with the retinal map 47 for the current observer. In this embodiment, this comparison is performed by performing a two dimensional correlation of the current retinal image and the retinal map 47. The results of this comparison are then passed to the controller 49, from which the observer's direction of gaze is determined. In this embodiment, this information is then passed to an auto-focus control unit 55, which operates to control the automatic focusing of the objective lens 3, so that the part of the object which the observer is currently looking at is in focus.

As shown in FIG. 2, the controller 49 is also connected to an illumination control unit 57, which is operable to control the illumination source 25. The reason for this will now be explained. In FIG. 1, the illumination source 25 is shown to be effectively on the same optical axis as the microscope 1. As a result, light from the source 25 which reflects off the cornea 15 (known as the cornea highlight or glint) will obscure the retinal image which is formed at the image plane 9. Therefore, as shown in FIG. 4, in this embodiment a source having six light emitting portions 61-1 to 61-6 which are arrayed around the optical axis is used. In operation, only those light emitting portions which do not cause cornea highlights in the retinal image (for the current direction of gaze) are used at any given time. Which ones should be turned off for a given direction of gaze can either be determined in advance during the calibration routine or can be determined in real time by monitoring for the presence of cornea highlights in the current retinal image. In this embodiment, the observer's direction of gaze is determined fifty times a second and the latter approach is used to control which light emitting portions should be turned off.

The illumination source 25 preferably operates to generate light at a wavelength in the region of 800 to 950 nm. This is because the transmittance of the ocular media and the reflectance of the retina at these wavelengths are both high. These wavelengths are also invisible to the human eye and should not result in any reduction of pupil size or reduction in the quality of the image observed through the microscope. However, as those skilled in the art will appreciate, illumination sources which operate at other wavelengths of light could be used. In this embodiment, the illumination source 25 comprises a high power 850 nm LED, which is operable to give about 0.2 mW at the front surface of the eye, which is well within current eye safety recommendations.

As those skilled in the art will appreciate, the above described eye tracking technique works well in this microscope application because the observer's eye is always focused at the intermediate image plane 9. As a result, any light reflected from the retina will form a sharp image of the retina at this intermediate image plane 9. Therefore, by locating the sensor 29 at a plane which is conjugate to the intermediate image plane 9, with respect to the lens 31, results in the image of the retina being formed on the sensor 29.

This eye tracking technique is also advantageous because it is independent of head movement and gives a direct measure of the position of gaze of the observer without having to relate measurements to the size, shape or position of the eye (which are required with other eye tracking techniques which use light reflected from the surface of the eye to determine the direction of gaze).

Alternative Embodiments

A number of modifications and alternative embodiments will now be described with reference to FIGS. 5 to 9.

Figure 5:
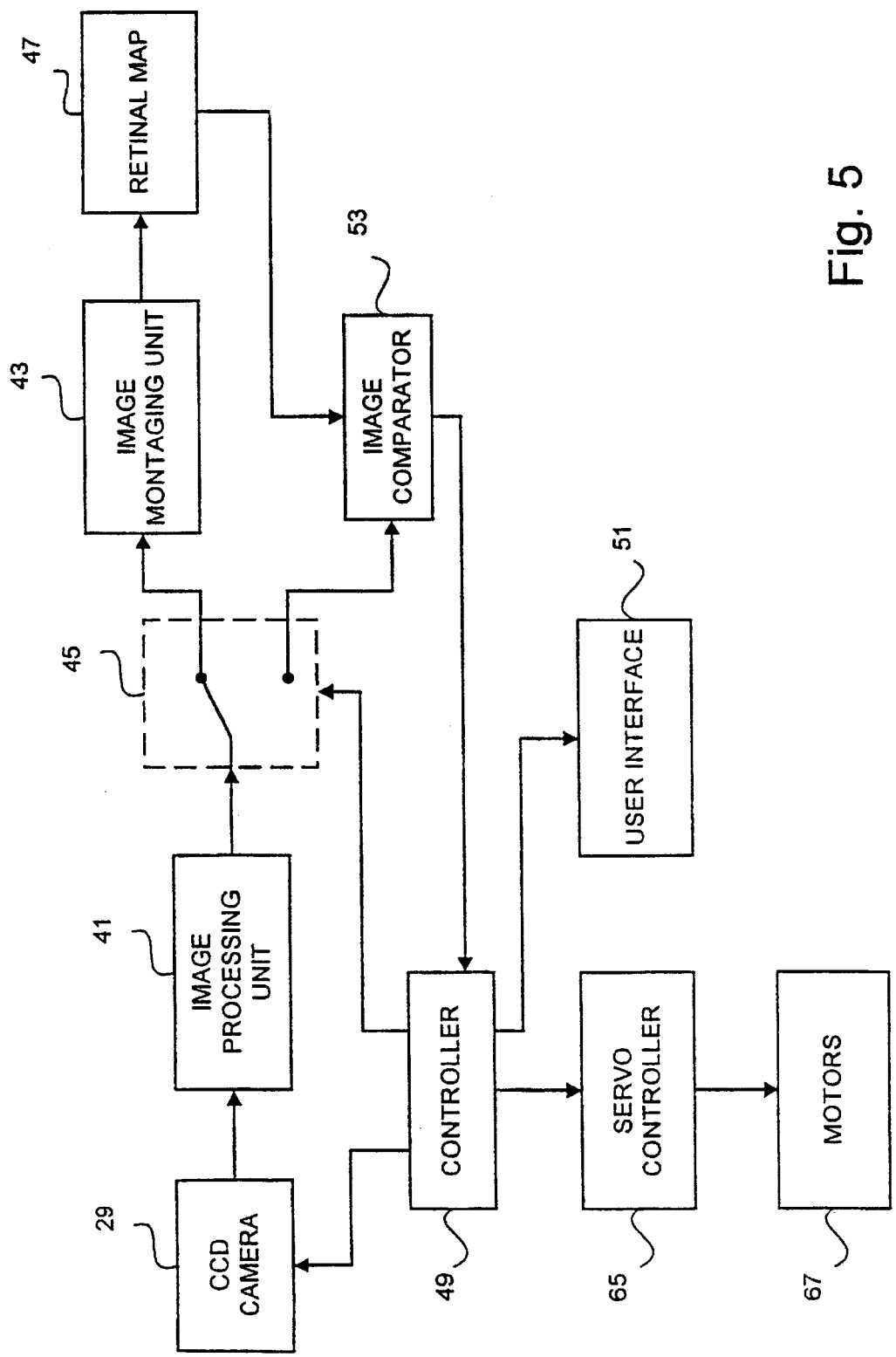
FIG. 5 is a block diagram illustrating the electronic components of an optical instrument embodying the present invention.

In the above embodiment, the direction of gaze information was used to control the automatic focusing of the microscope 1. As those skilled in the art will appreciate, the direction of gaze information can be used for other purposes. FIG. 5 shows the processing blocks used in an embodiment where the gaze information is used to control the movement of the microscope 1. Processing blocks which are the same as those described with reference to FIG. 2 have the same reference numeral. As shown, the only difference in this embodiment is the provision of a servo-controller 65 which is operable to receive the gaze information output by the controller 49 and in response thereto, is operable to control the operation of a number of motors 67 which move the microscope over the object being viewed.

Figure 6:
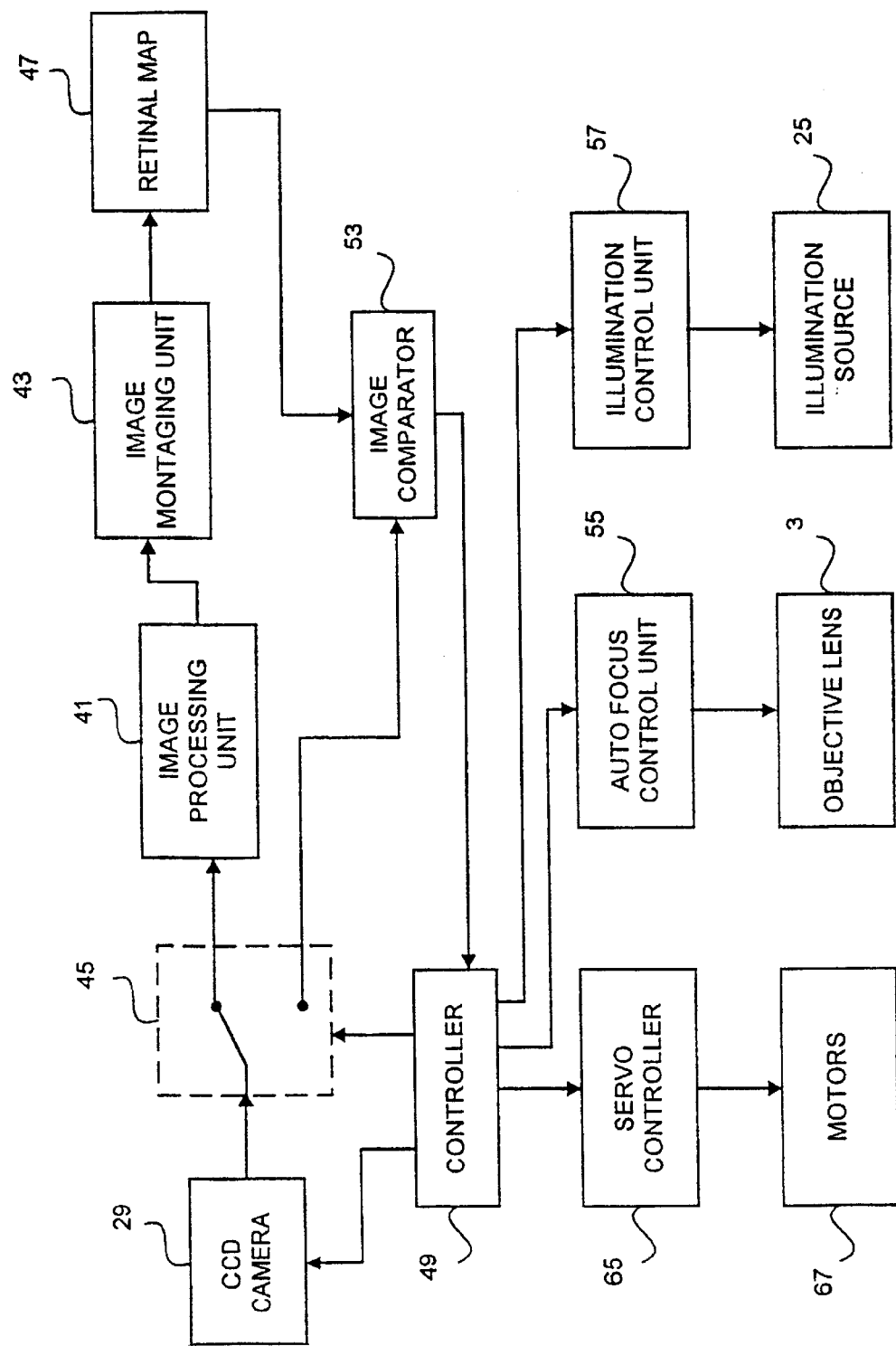
FIG. 6 is a block diagram illustrating the electronic components of an optical instrument embodying the present invention.

FIG. 6 shows the form of the processing and control electronics used in a further embodiment of the invention. As shown in FIG. 6, in this embodiment, only the retinal images used to generate the retinal map 47 are processed by the image processing unit 41. Therefore, during the normal mode of operation of the microscope, the image comparator 53 is operable to compare the current retinal image output by the sensor 29 with the retinal map 47. Additionally, as shown in FIG. 6, the direction of gaze information which is determined is used to control the positioning of the microscope and the focusing of the objective lens 3. The embodiment illustrated in FIG. 6 illustrates that it is not essential to process the retinal images generated by the sensor 29 in order to determine the direction of gaze. However, the preferred embodiment does process the retinal images in order to reduce the amount of data which needs to be compared by the image comparator 53.

Figure 7:
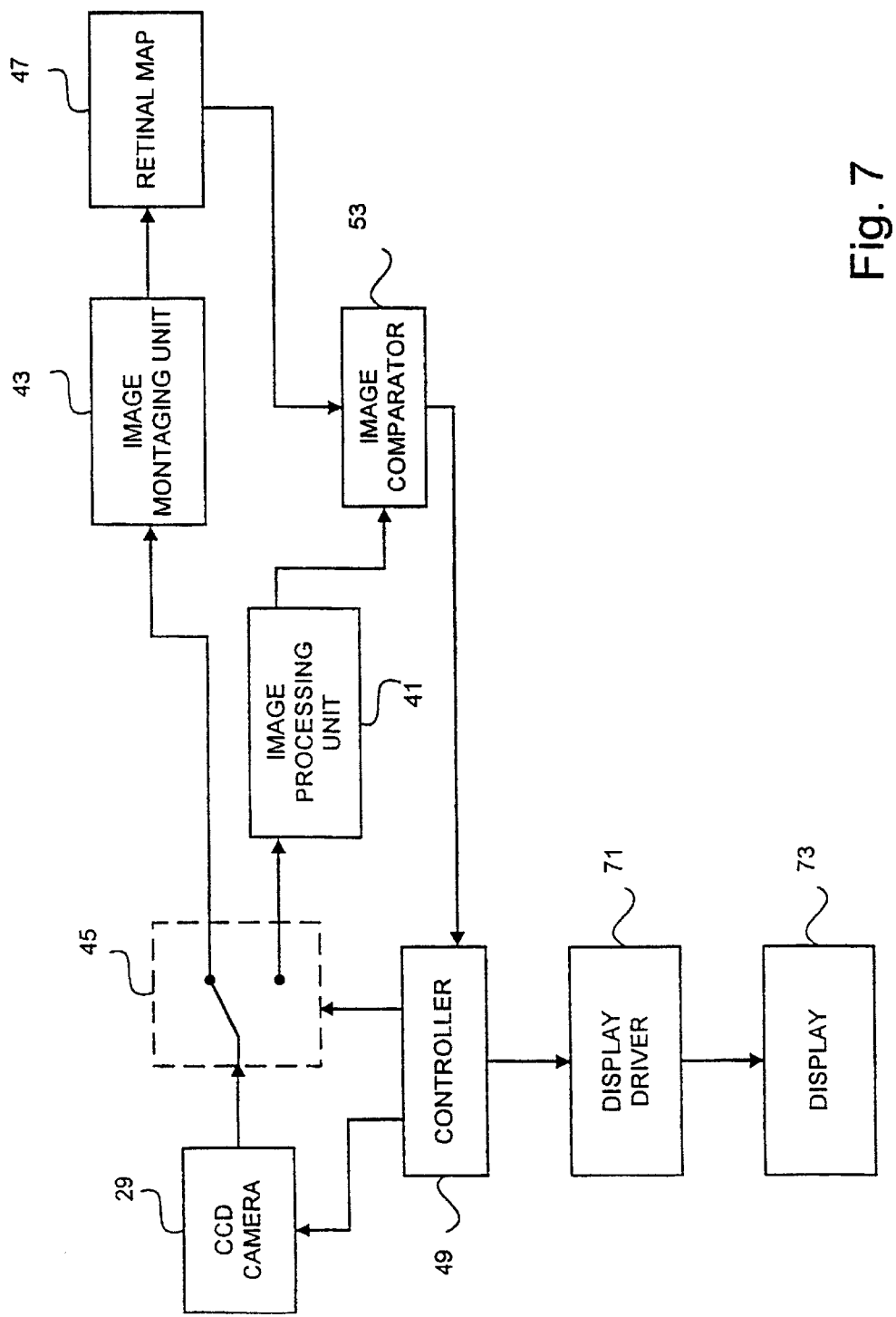
FIG. 7 is a block diagram illustrating the electronic components of an optical instrument embodying the present invention.

FIG. 7 shows the processing and control blocks used in yet another embodiment of the present invention. As shown, in this embodiment, only the retinal image generated during normal use of the microscope is processed by the image processing unit 43 before being compared with the retinal map 47 by the image comparator 53. In this embodiment the direction of gaze information obtained by the controller is passed to a display driver 71 which controls the display of menus on a display 73 which is located within the viewfinder of the microscope.

In the above embodiments, an illumination source having a plurality of light emitting portions which are effectively arrayed around the optical axis of the microscope was provided with only some of the light emitting portions being used at any one time. This arrangement was used in order to reduce the effect of cornea highlights. An alternative technique which could be used to overcome this problem is to use an illumination source which generates circularly polarised light. In particular, circularly polarised light reflected from the surface of the cornea will have its polarity reversed. However, light reflected from the retina is diffusely reflected and will therefore still contain a significant component in the original polarity. Consequently, by using a combination of a quarter-waveplate and polariser, it is possible to minimise the amount of light reflected back from the cornea reaching the sensor, thereby enabling the scattered light from the retina to be observed.

Another technique of solving the cornea highlight problem is to de focus the illumination beam so that it is not focused on the cornea. Whilst this technique is successful, it does result in a much smaller proportion of the retina being imaged, since the pupil restricts the light entering the eye.

Figure 8:
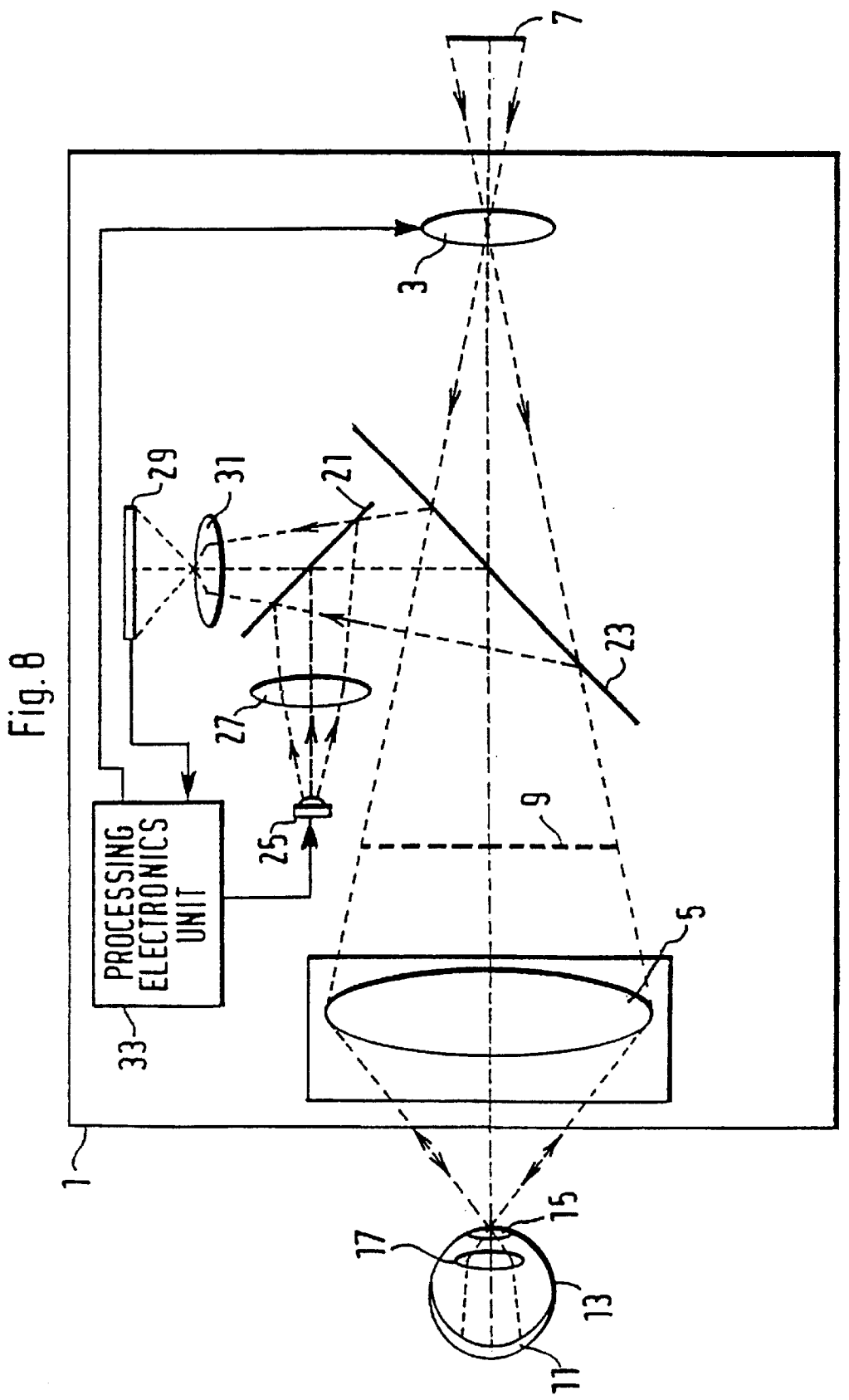
FIG. 8 is a schematic diagram of a microscope embodying the present invention.

In the above embodiments, the light for illuminating the retina was introduced after the eyepiece 5. FIG. 8 schematically illustrates the form of a microscope in which the illumination light is introduced before the eyepiece 5. In this embodiment, since the illumination light must pass through the eyepiece 5, the eyepiece 5 is preferably coated with an anti-reflection coating in order to minimise the direct reflection of the illumination light by the eyepiece 5.

In the above embodiments, an illumination source 25 was used to illuminate the retina of the observer's eye. As those skilled in the art will appreciate, in some applications, the light from the object being observed may be sufficient to illuminate the retina in which case, the illumination source 25 is not necessary.

In an improved embodiment of the invention the light of the illumination source is sent in pulses which are synchronized with the frequency of reading out the CCD sensor. This is to minimize the radiation on the user's retina.

The above embodiments have all related to an eye tracking technique for use in an optical microscope. As those skilled in the art will appreciate, the eye tracking technique described above can be used in many other optical instruments, such as cameras, telescopes etc. FIG. 9 shows a schematic diagram of a camera 81 which employs the eye tracking technique discussed above. As shown, the camera 81 comprises an objective lens 3 for focusing the object onto the intermediate image plane. However, in a camera, a real image is generated at the intermediate image plane by locating a diffusing glass screen 83 at the intermediate plane. The real image formed on the diffusing glass screen 83 is then viewed by the observer through the eyepiece 5 and a prism 85 which operates to reoriented the image the right way up. The camera also has a mirror 87 which can be moved up or down so that the light from the object is focused onto the film 89. The remaining components of the eye tracking system are the same as those used in the microscope embodiments described above and will not, therefore, be described again. It should, however, be noted that, in this embodiment, the sensor 29 and lens 31 are located in front of the diffusing glass screen 83, because the retinal image cannot pass through the diffusing glass plate 83. However, this is not important, since the sensor 29 is still located at a plane which is conjugate to the intermediate image plane.

In the above embodiments, the blood vessels in the retinal surface were used to identify the direction of gaze of the observer. As those skilled in the art will appreciate, other features of the retina can be used. For example, the location of the fovea can be used instead. However, since this requires a relatively high magnification, the use of the blood vessels is preferred, since these are more easily recognizable features.

In the above embodiment, the processing electronics determines the observer's direction of gaze 50 times per second. As a result, once the system has determined the current direction of gaze, it can use this information to reduce the amount of processing required to compare the current retinal image with the retinal map. In particular, it can use the last obtained direction of gaze to identify the portion of the retinal map which corresponds to the current retinal image and then use this part of the retinal map as a starting point.

In the above embodiments, a retinal map of each observer's retina had to be obtained first—preferably—during a calibration routine before that user can use the microscope. In an alternative embodiment, the retinal maps from a number of users can be combined to form a master template which models the common features of the retinal images of the training users. This master template can then be used for any user without the new user having to go through the calibration routine. Whilst this embodiment provides the advantage that the template is user independent, it suffers from the problem that the system will only be as good as the template.

In the above embodiments, the system automatically changed the focus of the objective lens if the observer's direction of gaze moved to a position in the field of view which was out of focus. In some applications, such an automatic, change of the focus may not be desired. In this case, the processing electronics may be arranged so that the automatic focusing only changes either if the user remains focused at the, same point for a predetermined length of time or if the observer inputs a control command signalling that he wishes the focus to be changed.

In the above embodiments, a beam splitter was used to effectively place the sensor and the sensor lens on the axis of the microscope. As those skilled in the art will appreciate, it is not essential to use such a beam splitter. For example, the sensor and the sensor lens can be located at an angle to the optical axis of the microscope, provided the sensor can still "see" the intermediate plane. Alternatively still, if the sensor is relatively small compared to the diameter of the objective lens, then the sensor can be placed along the axis of the objective lens. However, this embodiment is not preferred because it reduces the amount of light entering the observer's eye.

Instead of using the beamsplitter 23 a variant of this embodiment could be to have the sensor 29 look at the intermediate image plane 9 through the eye piece 5 and to use the backside of the beamsplitter 21 for reflecting the image of the retina to the opposite side of the light source 25. There a modified lens 31 and the sensor 29 would be arranged in the place of the dashed line 9 a part transparent mirror would be placed in order to reflect the image of the retina through the eye piece 5 into the sensor 29.

In the above embodiments, a single optical path has been illustrated through the optical instruments. As those skilled in the art will appreciate, where there are two optical paths (one for each eye) a similar eye tracking system could be provided in the other optical path. Alternatively, if the optical instrument allows the observer to view the object with both eyes, then a single selectable eye tracking system could be provided.

However two eye tracking systems (one in each optical path) would also allow for an automatic motorized adjustment of the two eye pieces towards each other with respect to the distance of the user's eyes. Also it would allow to always have the dominant eye of a user being tracked, since the movement of the dominant eye may be detected by comparing the movements of both eyes.

In the above embodiment, the comparison of the current retinal image output by the sensor with the retinal map is performed using a two-dimensional correlation technique. As those skilled in the art will appreciate, other comparison techniques can be employed. For example, the "active shape models" developed by Cootes et al at the University of Manchester can be used to model the characteristic features in the retina. The comparison would then involve matching similar shape models generated for the current retinal image with the stored shape models for the retinal map. The paper entitled "Use of Active Shape Models for Locating Structures in Medical Images" describes how these shape models can model structures in the human body for subsequent identification purposes. The content of this paper is incorporated herein by reference as well as the content of the PCT applications mentioned before.

Further embodiments will be apparent to those skilled in the art. The above embodiments and modifications have been given by way of example only and, as those skilled in the art will appreciate, the modifications made to some of the embodiments will be applicable to other embodiments.

"Comprising" in the claims means "containing" also.

What is claimed is:

1. A microscope for forming a viewable image of an object, comprising:
    an objective lens for forming a viewable image of the object at an image plane;
    an eye sensor for sensing a direction of gaze of a user viewing the viewable image; and
    means for adjusting a controllable function of said microscope in dependence upon the sensed direction of gaze;
    characterised in that said eye sensor comprises:
        (i) a sensor lens for focusing light reflected from the retina of the user;
        (ii) an imaging transducer located at a plane which when the user views said viewable image, is commonly conjugate with said image plane to the retina of the user's eye, for generating an electrical image signal of a portion of the user's retina;
        (iii) a memory for storing retinal image information of the user; and
        (iv) comparing means for comparing signals representative of the retinal image signal generated by said imaging transducer with said stored retinal image information to generate gaze information indicative of the direction of gaze of the user.

2. The microscope according to claim 1 further comprising an eyepiece through which the user can view said viewable image, and wherein said eyepiece comprises a lens system for increasing an apparent field of view of the microscope.

3. The microscope according to claim 1 or 2, wherein said sensor lens and said imaging transducer are located off an optical axis of said microscope.

4. The microscope according to claim 3, further comprising a beam splitter for reflecting the light reflected from the retina onto said sensor lens and said imaging transducer.

5. The microscope according to claim 2, further comprising an illumination source for illuminating the user's eye and an illumination lens for focusing the light from the illumination source.

6. The microscope according to claim 5, wherein said illumination lens is operable, in use, to focus tie light from the illumination source onto the cornea of the user's eye.

7. The microscope according to claim 5, wherein said illumination source is operable to generate light having a wavelength in the range of about 800 nm to about 950 nm.

8. The microscope according to claim 7, wherein said illumination source comprises an 850 nm LED.

9. The microscope according to any of claims 5 to 8, wherein said illumination source is located at an angle to an optical axis of the microscope.

10. The microscope according to claim 9, further comprising a beam splitter located on the optical axis of the microscope for reflecting the light from the illumination source into the eye.

11. The microscope according to claim 5, wherein said illumination source is operable to illuminate the eye through the eyepiece.

12. The microscope according to claim 11, wherein said eyepiece comprises an anti-reflective coating for preventing light from the source from being reflected from the eyepiece into the imaging transducer.

13. The microscope according to claim 5, wherein said illumination source comprises a plurality of light emitting portions which are operable to illuminate the user's eye at different angles.

14. The microscope according to claim 13, further comprising control means for selectively causing one or more of said light emitting portions to emit light.

15. The microscope according to claim 14, wherein said control means selects said one or more portions in dependence upon the direction of gaze of the user.

16. The microscope according to claim 14, wherein said control means selects said one or more portions in dependence upon the retinal image signal output by said imaging transducer.

17. The microscope according to claim 5, wherein said imaging transducer is operable to output a retinal image signal at a frequency between ten and fifty times per second.

18. The microscope according to claim 17, wherein the illumination source is operable to send light in pulses which are synchronised with said imaging transducer frequency.

19. The microscope according to claim 2, further comprising a half silvered minor in an intermediate image plane in order to reflect a retinal image trough the eyepiece.

20. The microscope according to claim 2, wherein said microscope includes two stereo beam paths each having an eyepiece associated therewith wherein said controllable function is an adjustment of a distance between the eyepieces to accommodate the interpupillary distance of a user's eyes.

21. The microscope according to claim 1, wherein said imaging transducer comprises a two-dimensional CCD sensor.

22. The microscope according to claim 1, further comprising means for processing the retinal image signal to highlight characteristic features in the retinal image.

23. The microscope according to claim 22, wherein said characteristic features include blood vessels.

24. The microscope according to claim 22 or 23 wherein said processing means comprises edge detection means for detecting edges in the retinal image.

25. The microscope according to claim 1, wherein said stored retinal image information comprises a map of the user's retina.

26. The microscope according to claim 25, wherein said retinal map is generated in advance during a calibration routine, in which the user looks at different preselected locations in the field of view of the microscope and in which the imaging transducer generates a retinal image for each of the preselected locations, from which the retinal map for the user is determined.

27. The microscope according to claim 1, wherein said controllable function is an automatic focusing of the objective lens so that a point in the field of view which the user is looking at is in focus.

28. The microscope according to claim 1, wherein said controllable function is the content of a display which is optically superimposed on the field of view of the microscope.

29. The microscope according to claim 1, wherein said imaging transducer is located at a plane conjugate to said image plane with respect to said sensor lens.

30. The microscope according to claim 1, wherein said controllable function is movement of the microscope over the object being viewed.

31. A microscope for forming a viewable image of an object, comprising:
    an objective lens for forming a viewable image of the object at an image plane;
    an eye sensor for sensing a direction of gaze of a user viewing the viewable image; and
    means for adjusting a controllable function of said microscope in dependence upon the sensed direction of gaze;
    characterised in that said eye sensor comprises:
        (i) a sensor lens for focusing light reflected from the retina of the user;
        an imaging transducer located at a plant conjugate to said image plane with respect to said sensor lens for generating an electrical image signal of a portion of the user's retina;
        (iii) a memory for storing retinal image information of the user; and
        (iv) comparing means for comparing signals representative of the retinal image signal generated by said imaging transducer with said stored retinal image information to generate gaze information indicative of the direction of gaze of the user's eye.

32. A microscope for forming a viewable image of an object, comprising:
    an objective lens for forming a viewable image of the object at an image plane;
    an eyepiece through which a user can view said viewable image;
    an eye sensor for sensing a direction of gaze of said user viewing said image through said eyepiece; and
    means for controlling a controllable function of said microscope in dependence upon the sensed direction of gaze;
    characterised in that said eye sensor comprises:
        (i) a sensor lens for focusing light reflected from the retina of the user;
        (ii) an imaging transducer located at a plane which, when the user views said viewable image, is commonly conjugate with said image plane to the retina of the user's eye, for generating an electrical image signal of the portion of the user's retina which can be seen through said eyepiece;

(iii) a memory for storing retinal image information; and (iv) comparing means for comparing signals representative of the retinal image signal generated by said imaging transducer with said stored retinal image information to generate gaze information indicative of the direction of gaze of the user.

33. A microscope for forming a viewable image of an object, comprising:

an objective lens for forming a viewable image of the object at an image plane;

an eye sensor for sensing a direction of gaze of a user viewing the viewable image; and means for adjusting a controllable function of said microscope in dependence upon the sensed direction of gaze;

characterised in that said eye sensor comprises:

(i) a sensor lens for focusing light reflected from the retina of the user;

(ii) an imaging transducer located at a plane which, when the user views said viewable image, is commonly conjugate with said image plane to the retina of the user's eye, for generating an electrical image signal of the pardon of the user's retina which is imaged on said transducer by said sensor lens;

(iii) a memory for storing retinal image information of the user; and (iv) comparing means for comparing signals representative of the retinal image signal generated by said imaging transducer with said stored retinal image information to generate gaze information indicative of the direction of gaze of the user.

34. A method of operating a microscope for forming viewable image of an object, comprising the steps of:

providing an objective lens for forming a viewable image of the object at an image plane;

sensing a direction of gaze of a user viewing the viewable image; and controlling a controllable function of the microscope in dependence upon the sensed direction of gaze;

characterized in that said sensing step comprises the steps of:

(i) using a sensor lens to focus light reflected from the retina of the user (ii) providing an imaging transducer located at a plane which, when the user views said viewable image, is commonly conjugate with said image plant to the retina of the user's eye, for generating an electrical signal of a portion of the user's retina; and (iii) comparing signals representative of the retina image signal generated by the imaging transducer with stored retinal image information to generate gaze information indicative of the direction of gaze of the user.

35. An optical instrument for forming a viewable image of an object, comprising:

an objective lens for forming a viewable image of the object at in image plane;

an eye sensor for sensing a direction of gaze of a user viewing the viewable image;

means for adjusting a controllable function of said optical instrument in dependence upon the sensed direction of gaze; and an eyepiece through which the user can view said viewable image, said eyepiece comprising a lens system for increasing an apparent field of view of the optical instrument;

characterised in that said eye sensor comprises:

(i) an illumination source for illuminating the user's eye and an illumination lens for focusing the light from the illumination source, wherein said illumination source comprises a plurality of light emitting portions which are operable to illuminate the uses eye at different angles;

(ii) control means for selectively causing one or more of said light emitting portions to emit light in dependence upon the direction of gaze of the user;

(iii) a sensor lens for focusing light reflected from the retina of the user, (iv) an imaging transducer located, at a plane which, when the user views said viewable image, is commonly conjugate with said image plane to the retina of the uses eye, for generating an electrical image signal of a portion of the user's retina;

(v) a memory for storing retinal i image information of the user; and (vi) comparing means for comparing signals representative of the retina image signal generated by said imaging transducer with said stored retina image information to generate gaze information indicative of the direction of gaze of the user.

36. An optical instrument for forming a viewable image of an object, comprising:

an objective lens for forming a viewable image of the object at an image plane;

an eye sensor for sensing a direction of gaze of a user viewing the viewable image; and means for adjusting a controllable function of said optical instrument in dependence upon the sensed direction of gaze;

characterized in that said eye sensor comprises:

(i) a sensor lens for focusing light reflected from the retina of the user;

(ii) an imaging transducer located at a plane which, when the user views said viewable image, is commonly conjugate with said image plane to the retina of the user's eye, for generating in electrical image signal of a portion of the user's retina;

(iii) means for processing the retinal image signal to highlight characteristic features in the retinal image, wherein said processing means comprises edge detection means for detecting edges in the retinal image;

(iv) a memory for storing retinal image information of the user; and (v) comparing means for comparing signals representative of the retinal image signal generated by said imaging transducer with said stoked retinal image information to generate gaze information indicative of the direction of gaze of the user.

37. The instrument according to claim 36, wherein said characteristic features include blood vessels.

38. An optical instrument for forming a viewable image of an object, comprising:

an objective lens for forming a viewable image of the object at an image plant;

an eye sensor for sensing a direction of gaze of a user viewing the viewable image; and means for adjusting a controllable function of said optical instrument in dependence upon the sensed direction of gaze;

characterised in that said eye sensor comprises:
  (i) a sensor lens for focusing light reflected from the retina of the user;
  (ii) an imaging transducer located at a plane which, when the user views said viewable image, is commonly conjugate with said image plane to the retina of the user's eye, for generating an electrical image signal of a portion of the user's retina;
  (iii) a memory for storing retinal image information of the user, wherein said stored retinal image information comprises a map of the user's retina generated in advance during a calibration routine, in which the user looks at different preselected locations in the field of view of the instrument and in which the imaging transducer generates a retinal image for each of the preselected locations, from which the retinal map for the user is determined; and
  (iv) comparing means for comparing signals representative of the retinal image signal generated by said imaging transducer with said stored retinal image information to generate gaze information indicative of the direction of gaze of the user.

39. An optical instrument for forming a viewable image of an object, comprising:
  an objective lens for forming a viewable image of the object at an image plane;
  an eye sensor for sensing a direction of gaze of a user viewing the viewable image; and
  means for adjusting a controllable function of said optical instrument in dependence upon the sensed direction of gaze;
  characterised in that said eye sensor comprises:
    (i) a sensor lens for focusing light reflected from the retina of the user;
    (ii) an imaging transducer located at a plane which, when the user views said viewable image, is commonly conjugate with said imago plane to the retina of the user's eye, for generating an electrical image signal of a portion of the user's retina;
    (iii) a memory for storing retina image information of the user, and
    (iv) comparing means for comparing signals representative of the retinal image signal generated by said imaging transducer with said stared retinal image information to generate gaze information indicative of the direction of gaze of the user; and
  said optical instrument being farther characterised in that said controllable function is an automatic focusing of the objective lens so that a point in the field of view which the user is looking at is in focus.

40. The optical instrument according to claim 39, wherein said controllable function includes an automatic movement of the optical instrument over the object being viewed.

41. At optical instrument for forming a viewable image of an object, comprising;
  an objective lens for forming a viewable image of the object at an image plane
  an eye sensor for sensing a direction of gaze of a user viewing the viewable image;
  means for adjusting a controllable function of said optical instrument in dependence upon the sensed direction of gaze; and
  a of eyepieces through which the user can view said viewable image along stereo beam paths;
  characterised in that said eye sensor comprises:
    (i) a sensor lens for focusing light reflected from the retina of the user;
    (ii) an imaging transducer located at a plane which, when the user views said viewable image, is commonly conjugate with said image plane to the retina of the user's eye, for generating an electrical image signal of a portion of the user's retina;
    (iii) a memory for storing retinal image information of the user; and
    (iv) comparing means for comparing signals representative of the retinal image signal generated by said imaging transducer with said stored retinal image information to generate gaze information indicative of the direction of gaze of the user; and
  said optical instrument being further characterised in that said controllable function is an adjustment of a distance between the pair of eyepieces to accommodate the interpupillary distance of a user's eyes.

42. An optical instrument for forming a viewable image of an object, comprising:
  an objective lens for forming a viewable image of the object at an image plane;
  an eye sensor for sensing a direction of gaze of a user viewing the viewable image; and
  means for adjusting a controllable function of said optical instrument in dependence upon the sensed direction of gaze;
  characterised in that said eye sensor comprises:
    (i) a sensor lens for focusing light reflected from the retina of the user;
    (ii) an imaging transducer located at a plane which, when the user views said viewable image, is commonly conjugate with said image plane to the retina of the user's eye, for generating an electrical image signal of a portion of the user's retina;
    (iii) a memory for storing retinal image information of the user; and
    (iv) comparing means for comparing signals representative of the retinal image signal generated by said imaging transducer with said stored retinal image information to generate gaze information indicative of the direction of gaze of the user; and
  said optical instrument being further characterised in that said controllable function is the content of a display which is optically superimposed on the field of view of the instrument.

* * * * *